United States Patent
Schwaben et al.

(10) Patent No.: US 12,281,063 B2
(45) Date of Patent: Apr. 22, 2025

(54) LOW-PRESSURE HYDROFORMYLATION OF DIISOBUTENE

(71) Applicant: BASF SE, Ludwigshafen am Rhein (DE)

(72) Inventors: Jonas Schwaben, Ludwigshafen am Rhein (DE); Rocco Paciello, Ludwigshafen am Rhein (DE); Rainer Papp, Ludwigshafen am Rhein (DE)

(73) Assignee: BASF SE

( * ) Notice: Subject to any disclaimer, the term of this patent is extended or adjusted under 35 U.S.C. 154(b) by 440 days.

(21) Appl. No.: 17/798,607

(22) PCT Filed: Feb. 1, 2021

(86) PCT No.: PCT/EP2021/052241
§ 371 (c)(1),
(2) Date: Aug. 10, 2022

(87) PCT Pub. No.: WO2021/160448
PCT Pub. Date: Aug. 19, 2021

(65) Prior Publication Data
US 2023/0192580 A1    Jun. 22, 2023

(30) Foreign Application Priority Data

Feb. 11, 2020 (EP) .................... 20156540

(51) Int. Cl.
*C07C 45/50* (2006.01)
(52) U.S. Cl.
CPC ................. *C07C 45/505* (2013.01)
(58) Field of Classification Search
CPC ................................. C07C 45/505
See application file for complete search history.

(56) References Cited

U.S. PATENT DOCUMENTS

| | | | |
|---|---|---|---|
| 2,554,251 A | 5/1951 | Hudson | |
| 4,467,116 A | 8/1984 | Van Leeuwen et al. | |

(Continued)

FOREIGN PATENT DOCUMENTS

| | | |
|---|---|---|
| DE | 19914260 A1 | 10/2000 |
| EP | 0423769 A2 | 4/1991 |

(Continued)

OTHER PUBLICATIONS

Kubis, et al., "A Comparative In Situ HP-FTIR Spectroscopic Study of Bi- and Monodentate Phosphite-Modified Hydroformylation", ChemCatChem, vol. 2, Issue 3, Mar. 3, 2010, pp. 287-295.
Sicherheitsdatenblatt der Fa. BASF SE fur das Produkt "Isononanal" (Safety data sheet from BASF SE for the product "Isononanal"), Version 2.0, Feb. 2, 2024, pp. 1-15.
Versuchsbericht der Evonik Oxeno Gmbh & Co. KG betreffend den Einspruch gegen das europaische Patent EP 4103571 B1 (Test report from Evonik Oxeno Gmbh & Co. KG regarding the opposition to the European patent EP 4103571 B1), Jul. 12, 2024, pp. 1-2.
Wikipedia-Exzerpt zu "Hydroformylierung" (Wikipedia excerpt on "Hydroformylation"), Last edited on May 23, 2023, pp. 1-11.
Wikipedia-Exzerpt zu "Isoocten" (Wikipedia excerpt on "Isoocten"), Last edited on Jan. 30, 2023, pp. 1-3.
International Preliminary Report on Patentability received for PCT Patent Application No. PCT/EP2021/052241, mailed on May 19, 2022, 11 pages (6 pages of English Translation and 5 pages of Original Document).

(Continued)

*Primary Examiner* — Sikarl A Witherspoon
(74) *Attorney, Agent, or Firm* — Faegre Drinker Biddle & Reath LLP

(57) ABSTRACT

A hydroformylation process for preparing 3,5,5-trimethylhexanal comprising reacting 2,4,4-trimethylpent-2-ene with $H_2$ and CO in a reaction zone in the presence of one or more free organophosphite ligands of the general formula (I)

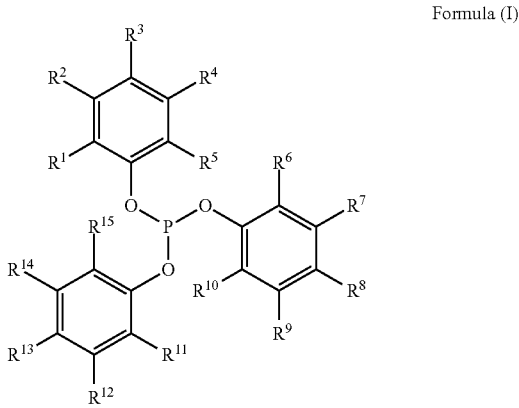

Formula (I)

wherein $R^1$, $R^2$, $R^3$, $R^4$ and $R^5$ are each independently H, $C_1$- to $C_9$-alkyl or $C_1$- to $C_9$-alkoxy and $R^1$, $R^2$, $R^3$, $R^4$ and $R^5$ are not H at the same time, and $R^6$, $R^7$, $R^8$, $R^9$ and $R^{10}$ are each independently H, $C_1$- to $C_9$-alkyl or $C_1$- to $C_9$-alkoxy and Re, $R^7$, $R^8$, $R^9$ and $R^{10}$ are not H at the same time, and $R^{11}$, $R^{12}$, $R^{13}$, $R^{14}$ and $R^{15}$ are each independently H, $C_1$- to $C_9$-alkyl or $C_1$- to $C_9$-alkoxy and $R^{11}$, $R^{12}$, $R^{13}$, $R^{14}$ and $R^{15}$ are not H at the same time, and a homogeneous rhodium catalyst complexed with one or more organophosphite ligands of the general formula (I) at a pressure of 1 to 100 bar abs and a temperature of from 50 to 200° C.

14 Claims, No Drawings

(56) References Cited

U.S. PATENT DOCUMENTS

| | | | |
|---|---|---|---|
| 4,625,068 A * | 11/1986 | Young | B01J 31/2404 568/454 |
| 4,778,929 A | 10/1988 | Zehner et al. | |
| 5,064,794 A | 11/1991 | Drake | |
| 5,728,893 A | 3/1998 | Becker et al. | |
| 6,403,837 B1 | 6/2002 | Hess et al. | |
| 6,700,021 B2 | 3/2004 | Bohnen et al. | |
| 2004/0054246 A1 | 3/2004 | Nierlich et al. | |
| 2011/0065970 A1 | 3/2011 | Cross, Jr. | |
| 2014/0128652 A1 | 5/2014 | Yamakawa et al. | |
| 2015/0336861 A1 | 11/2015 | Geilen et al. | |
| 2018/0290132 A1 | 10/2018 | Kim et al. | |

FOREIGN PATENT DOCUMENTS

| | | |
|---|---|---|
| EP | 0846095 A1 | 6/1998 |
| EP | 1099678 A1 | 5/2001 |
| EP | 1114017 A1 | 7/2001 |
| EP | 1231198 A1 | 8/2002 |
| EP | 1255720 A2 | 11/2002 |
| EP | 1360160 A1 | 11/2003 |
| EP | 2836474 A1 | 2/2015 |
| EP | 2947064 A1 | 11/2015 |
| EP | 3466540 A1 | 4/2019 |
| EP | 3482827 A1 | 5/2019 |
| RU | 2270828 C1 | 2/2006 |
| WO | 03/95406 A1 | 11/2003 |
| WO | 2010/097376 A1 | 9/2010 |
| WO | 2013/153136 A1 | 10/2013 |
| WO | 2018/221830 A1 | 12/2018 |
| WO | 2021/160448 A1 | 8/2021 |

OTHER PUBLICATIONS

International Search Report and Written Opinion received for PCT Patent Application No. PCT/EP2021/052241, mailed on Feb. 26, 2021, 11 pages (2 pages of English Translation and 9 pages of Original Document).

Bahrmann, et al., "Oxo Synthesis", Ullmann's Encyclopedia of Industrial Chemistry, ed. Ley, et al., Jan. 15, 2013, pp. 1-8.

Borner, et al., "Process for the catalytic preparation of aldehydes from olefins using ligand mixtures", Database CAPLUS, retrieved from STN Database accession No. 2001: 356241, XP055708745, 2001, 7 pages.

European Search Report for EP Patent Application No. 20156540.5, Issued on Jul. 9, 2020, 3 pages.

Jürgen Falbe, "Chapter 10: Industrial Hydroformylation Operations", Carbon Monoxide in Organic Synthesis, Jun. 1970, pp. 70-74.

* cited by examiner

LOW-PRESSURE HYDROFORMYLATION OF DIISOBUTENE

CROSS-REFERENCE TO RELATED APPLICATIONS

This application is a national stage application (under 35 U.S.C. § 371) of PCT/EP2021/052241, filed Feb. 1, 2021, which claims benefit of European Application No. 20156540.5, filed Feb. 11, 2020, both of which are incorporated herein by reference in their entirety.

DESCRIPTION $C_9$-aldehydes are important intermediates in the chemical industry. The $C_9$-alcohols obtained by hydrogenation of $C_9$-aldehydes are used, for example, in the manufacture of plasticizers, while the $C_9$-carboxylic acids obtained by oxidation of $C_9$-alcohols and/or $C_9$-aldehydes are used, for example, in the manufacture of lubricants, including for use in refrigeration systems, in the manufacture of cosmetics or in the production of metal salts. Such metal salts are used, for example, as paint driers or PVC stabilizers.

$C_9$-aldehydes are produced industrially by hydroformylation of $C_8$-olefins. The $C_8$-olefins used for hydroformylation are typically $C_8$-isomeric mixtures, such as are obtained by dimerization of isobutene. Processes for the dimerization of isobutene are disclosed, for example, in US 2014/0128652 A1, RU 2270828 C1, US 2011/0065970 A1, U.S. Pat. No. 5,064,794 A1 or EP 1360160 A1. The main products obtained by dimerization of isobutene are usually 2,4,4-trimethylpent-1-ene and 2,4,4-trimethylpent-2-ene. 2,3,4-Trimethylpentenes are by-products which may form, for example, due to skeletal isomerization reactions during dimerization of isobutene.

Due to the lower reactivity of 2,4,4-trimethylpent-2-ene compared to 2,4,4-trimethylpent-1-ene, the hydroformylation of mixtures of 2,4,4-trimethylpent-1-ene and 2,4,4-trimethylpent-2-ene results in accumulation of 2,4,4-trimethylpent-2-ene in the reaction system. This reduces the space-time yield and it is necessary to separate the 2,4,4-trimethylpent-2-ene from the reaction system.

In order to use the separated 2,4,4-trimethylpent-2-ene productively in the hydroformylation, this can be isomerized, for example to 2,4,4-trimethylpent-1-ene, and then be recycled to the hydroformylation reaction. A process for the isomerization of 2,4,4-trimethylpent-2-ene under acid catalysis is described, for example, in U.S. Pat. No. 2,554,251. However, this represents an additional process step and is therefore not desirable.

In order to avoid separation of 2,4,4-trimethylpent-2-ene from the reaction system and to hydroformylate 2,4,4-trimethylpent-2-ene, the hydroformylation can be carried out at high pressures using non-ligand-modified rhodium or cobalt complexes, or using ligand-modified cobalt complexes having high isomerization activity (Shell process).

Processes for high-pressure hydroformylation and processes for hydroformylation using ligand-modified cobalt complexes are described, for example, in Ullmann's Encyclopedia of Industrial Chemistry, Oxo Synthesis, DOI: 10.1002/14356007.a18_312.pub2 or in J. Falbe, Carbon Monoxide in Organic Synthesis, Springer-Verlag, Berlin Heidelberg, New York, 1970, pages 70 to 74. Disadvantages of the processes mentioned are the high pressures specified and/or the high rates of hydrogenation of the aldehydes formed to the corresponding alcohols. The resulting complex product mixtures have to be laboriously separated downstream.

U.S. Pat. No. 6,403,837 describes a process for the rhodium-catalyzed hydroformylation of di-n-butene at pressures which are preferably in the range of 10 to 60 bar using a combination of organophosphonite and organophosphite ligands.

U.S. Pat. No. 4,467,116 describes the rhodium-catalyzed hydroformylation of β-alkyl-substituted acyclic α-olefins at pressures of 2 to 50 bar using organophosphite ligands.

However, a process for the rhodium-catalyzed hydroformylation of 2,4,4-trimethylpent-2-ene to 3,5,5-trimethylhexanal under mild conditions and using organophosphite ligands which affords high yields over time is not known in the prior art.

The object of the present invention was to provide a rhodium-catalyzed process in which 2,4,4-trimethylpent-2-ene may be hydroformylated in the presence of organophosphite ligands under mild conditions in high yields over time to give 3,5,5-trimethylhexanal. The process should also be able to hydroformylate mixtures of 2,4,4-trimethylpent-1-ene and 2,4,4-trimethylpent-2-ene under mild conditions in high yields over time to give 3,5,5-trimethylhexanal. The process according to the invention should also be characterized by high stability of the organophosphite ligands used. This is intended to ensure that only a small amount of by-product formation occurs and, in the case of a continuous process regime, the ligands and/or the catalyst metal-ligand complexes can be recycled into the process. This also enables the process to have a long service life.

A high yield over time with respect to the hydroformylation of 2,4,4-trimethylpent-2-ene to 3,5,5-trimethylhexanal is achieved if a conversion of the starting material of ≥85% and a selectivity of ≥95% are attained within 10 hours.

A high yield over time with respect to the hydroformylation of 2,4,4-trimethylpent-1-ene to 3,5,5-trimethylhexanal is achieved if a conversion of the starting material of ≥95% and a selectivity of ≥95% are attained within 10 hours.

Mild conditions are present when the pressure at which the hydroformylation is carried out is 1 to 100 bar absolute, preferably 5 to 80 bar absolute, more preferably 5 to 55 bar absolute and particularly preferably 8 to 20 bar absolute and the temperature at which the hydroformylation is carried out is 50 to 200° C., preferably 80 to 150° C., and particularly preferably 90 to 120° C.

By-products are degradation products of the ligands and/or reaction products and/or conversion products from the reaction between the degradation products of the ligands and the aldehydes produced in the hydroformylation.

The object is achieved by a hydroformylation process for preparing 3,5,5-trimethylhexanal comprising reacting 2,4,4-trimethylpent-2-ene with $H_2$ and CO in a reaction zone in the presence of one or more free organophosphite ligands of the general formula (I)

Formula (I)

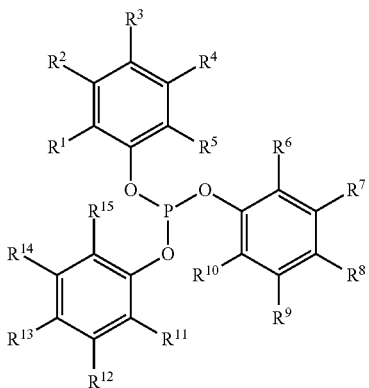

wherein,
$R^1$, $R^2$, $R^3$, $R^4$ and $R^5$ are each independently H, $C_1$- to $C_9$-alkyl or $C_1$- to $C_9$-alkoxy and $R^1$, $R^2$,
$R^3$, $R^4$ and $R^5$ are not H at the same time, and
$R^6$, $R^7$, $R^8$, $R^9$ and $R^{10}$ are each independently H, $C_1$- to $C_9$-alkyl or $C_1$- to $C_9$-alkoxy and $R^6$, $R^7$,
$R^8$, $R^9$ and $R^{10}$ are not H at the same time, and
$R^{11}$, $R^{12}$, $R^{13}$, $R^{14}$ and $R^{15}$ are each independently H, $C_1$- to $C_9$-alkyl or $C_1$- to $C_9$-alkoxy and $R^{11}$,
$R^{12}$, $R^{13}$, $R^{14}$ and $R^{15}$ are not H at the same time, and a homogeneous rhodium catalyst complexed with one or more organophosphite ligands of the general formula (I) at a pressure of 1 to 100 bar abs and a temperature of from 50 to 200° C.

In a compound of the general formula (I):

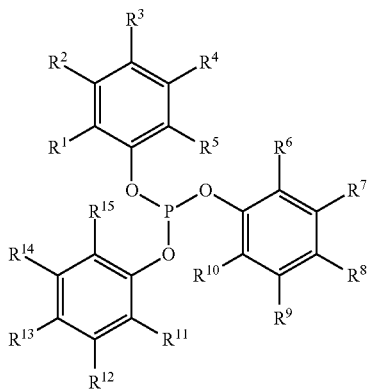

$R^1$, $R^2$, $R^3$, $R^4$ and $R^5$ are each independently H, $C_1$- to $C_9$-alkyl or $C_1$- to $C_9$-alkoxy, where $R^1$, $R^2$, $R^3$, $R^4$ and $R^5$ are not H at the same time. Preferably, $R^1$, $R^2$, $R^3$, $R^4$ and $R^5$ are each independently H, $C_1$- to $C_4$-alkyl or $C_1$- to $C_4$-alkoxy, where $R^1$, $R^2$, $R^3$, $R^4$ and $R^5$ are not H at the same time.

$R^8$, $R^7$, $R^8$, $R^9$ and $R^{10}$ are each independently H, $C_1$- to $C_9$-alkyl or $C_1$- to $C_9$-alkoxy, where Re, $R^7$, $R^8$, R°and $R^{10}$ are not H at the same time. Preferably, $R^8$, $R^7$, $R^8$, $R^9$ and $R^{10}$ are each independently H, $C_1$- to $C_4$-alkyl or $C_1$- to $C_4$-alkoxy, where $R^8$, $R^7$, $R^8$, $R^9$ and $R^{10}$ are not H at the same time.

$R^{11}$, $R^{12}$, $R^{13}$, $R^{14}$ and $R^{15}$ are each independently H, $C_1$- to $C_9$-alkyl or $C_1$- to $C_9$-alkoxy, where $R^{11}$, $R^{12}$, $R^{13}$, $R^{14}$ and $R^{15}$ are not H at the same time. Preferably, $R^8$, $R^7$, $R^8$, $R^9$ and $R^{1\circ}$ are each independently H, $C_1$- to $C_4$-alkyl or $C_1$- to $C_4$-alkoxy, where $R^{11}$, $R^{12}$, $R^{13}$, $R^{14}$ and $R^{15}$ are not H at the same time.

In a preferred embodiment of the formula (I):
$R^1$, $R^3$ and $R^5$ are each independently H, $C_1$- to $C_9$-alkyl or $C_1$- to $C_9$-alkoxy, preferably H, $C_1$- to $C_4$-alkyl or $C_1$- to $C_4$-alkoxy and $R^2$ and $R^4$ are H, where $R^1$, $R^3$ and $R^5$ are not H at the same time, and $R^8$, $R^8$ and $R^{15}$ are each independently H, $C_1$- to $C_9$-alkyl or $C_1$- to $C_9$-alkoxy, preferably H, $C_1$- to $C_4$-alkyl or $C_1$- to $C_4$-alkoxy and $R^7$ and $R^9$ are H, where $R^6$, $R^8$ and $R^{1\circ}$ are not H at the same time, and $R^{11}$, $R^{13}$ and $R^{15}$ are each independently H, $C_1$- to $C_9$-alkyl or $C_1$- to $C_9$-alkoxy, preferably H, $C_1$- to $C_4$-alkyl or $C_1$- to $C_4$-alkoxy and $R^{12}$ and $R^{14}$ are H, where $R^{11}$, $R^{13}$ and $R^{15}$ are not H at the same time.

In a further preferred embodiment of the formula (I):
$R^1$ is $C_1$- to $C_9$-alkyl or $C_1$- to $C_9$-alkoxy, preferably $C_1$- to $C_4$-alkyl or $C_1$- to $C_4$-alkoxy, $R^3$ is H, $C_1$- to $C_9$-alkyl or $C_1$- to $C_9$-alkoxy, preferably H, $C_1$- to $C_4$-alkyl or $C_1$- to $C_4$-alkoxy and $R^2$, $R^4$ and $R^5$ are H, and $R^8$ is $C_1$- to $C_9$-alkyl or $C_1$- to $C_9$-alkoxy, preferably $C_1$- to $C_4$-alkyl or $C_1$- to $C_4$-alkoxy, $R^8$ is H, $C_1$- to $C_9$-alkyl or $C_1$- to $C_9$-alkoxy, preferably H, $C_1$- to $C_4$-alkyl or $C_1$- to $C_4$-alkoxy and $R^7$, $R^9$ and $R^{10}$ are H, and $R^{11}$ is $C_1$- to $C_9$-alkyl or $C_1$- to $C_9$-alkoxy, preferably $C_1$- to $C_4$-alkyl or $C_1$- to $C_4$-alkoxy, $R^{13}$ is H, $C_1$- to $C_9$-alkyl or $C_1$- to $C_9$-alkoxy, preferably H, $C_1$- to $C_4$-alkyl or $C_1$- to $C_4$-alkoxy and $R^{12}$, $R^{14}$ and $R^{15}$ are H.

In a further preferred embodiment of the formula (I):
$R^1$ and $R^3$ are $C_1$- to $C_9$-alkyl or $C_1$- to $C_9$-alkoxy, preferably $C_1$- to $C_4$-alkyl or $C_1$- to $C_4$-alkoxy and $R^2$, $R^4$ and $R^5$ are H, and $R^6$ and $R^8$ are $C_1$- to $C_9$-alkyl or $C_1$- to $C_9$-alkoxy, preferably $C_1$- to $C_4$-alkyl or $C_1$- to $C_4$-alkoxy and $R^7$, $R^9$ and $R^{10}$ are H, and $R^{11}$ and $R^{13}$ are $C_1$- to $C_9$-alkyl or $C_1$- to $C_9$-alkoxy, preferably $C_1$- to $C_4$-alkyl or $C_1$- to $C_4$-alkoxy and $R^{12}$, $R^{14}$ and $R^{15}$ are H, where $R^1$, $R^3$, $R^8$, $R^8$, $R^{11}$ and $R^{13}$ are the same.

In particularly preferred embodiments of the formula (I) are:

|  | $R^1$, $R^6$, $R^{11}$ | $R^3$, $R^8$, $R^{13}$ | $R^2$, $R^4$, $R^5$, $R^7$, $R^9$, $R^{10}$, $R^{12}$, $R^{14}$, $R^{15}$ |
|---|---|---|---|
| I) | Methyl | Methyl | H |
| II) | Methyl | H | H |
| III) | Ethyl | Ethyl | H |
| IV) | Ethyl | H | H |
| V) | n-Propyl | n-Propyl | H |
| VI) | n-Propyl | H | H |
| VII) | Isopropyl | Isopropyl | H |
| VIII) | Isopropyl | H | H |
| IX) | n-Butyl | n-Butyl | H |
| X) | n-Butyl | H | H |
| XI) | sec-Butyl | sec-Butyl | H |
| XII) | sec-Butyl | H | H |
| XIII) | Isobutyl | Isobutyl | H |
| XIV) | Isobutyl | H | H |
| XV) | tert-Butyl | tert-Butyl | H |
| XVI) | tert-Butyl | H | H |
| XVII) | Methoxy | Methoxy | H |
| XVIII) | Methoxy | H | H |
| XIX) | Ethoxy | Ethoxy | H |
| XX) | n-Propoxy | n-Propoxy | H |
| XXI) | n-Propoxy | H | H |
| XXII) | Isopropoxy | Isopropoxy | H |
| XXIII) | Isopropoxy | H | H |

-continued

| | $R^1, R^6, R^{11}$ | $R^3, R^8, R^{13}$ | $R^2, R^4, R^5, R^7, R^9,$ $R^{10}, R^{12}, R^{14}, R^{15}$ |
|---|---|---|---|
| XXIV) | n-Butoxy | n-Butoxy | H |
| XXV) | n-Butoxy | H | H |
| XXVI) | sec-Butoxy | sec-Butoxy | H |
| XXVII) | sec-Butoxy | H | H |
| XXVIII) | Isobutoxy | Isobutoxy | H |
| XXIX) | Isobutoxy | H | H |
| XXX) | tert-Butoxy | tert-Butoxy | H |
| XXXI) | tert-Butoxy | H | H |
| XXXII) | n-Nonyl | H | H |

In particular, preference is given to embodiments XV) and XVI).

$C_1$- to $C_9$-alkyl comprises straight-chain or branched $C_1$- to $C_9$-alkyl groups or cyclic $C_3$- to $C_9$-alkyl groups. Examples of $C_1$- to $C_9$-alkyl are methyl, ethyl, n-propyl, isopropyl, cyclopropyl, n-butyl, sec-butyl, isobutyl, tert-butyl, n-pentyl, 2-methylbutyl, 3-methylbutyl, cyclopentyl, n-hexyl, cyclohexyl, 2-methylpentyl, 3-methylpentyl, 4-methylpentyl, 3,3-dimethylbutyl, 2-ethylbutyl, n-heptyl, 2-methylhexyl, 2-ethylpentyl, 4-methylcyclohexyl, n-octyl, isooctyl or 2-ethylhexyl, n-nonyl or isononyl.

$C_1$- to $C_4$-alkyl comprises straight-chain or branched $C_1$- to $C_4$-alkyl groups or cyclic $C_3$-alkyl groups. $C_1$- to $C_4$-alkyl is, for example, methyl, ethyl, n-propyl, isopropyl, cyclopropyl, n-butyl, sec-butyl, isobutyl or tert-butyl.

$C_1$- to $C_9$-alkoxy comprises straight-chain or branched $C_1$- to $C_9$-alkoxy groups or cyclic $C_3$- to $C_8$-alkoxy groups. $C_1$- to $C_9$-alkoxy are, for example, methoxy, ethoxy, n-propoxy, isopropoxy, cyclopropoxy, n-butoxy, sec-butoxy, isobutoxy, tert-butoxy, n-pentoxy, 2-methylbutoxy, 3-methylbutoxy, cyclopentoxy, n-hexoxy, cyclohexoxy, 2-methylpentoxy, 3-methylpentoxy, 4-methylpentoxy, 3,3-dimethylbutoxy, 2-ethylbutoxy, n-heptoxy, 2-methylhexoxy, 2-ethylpentoxy, 4-methylcyclohexoxy, n-octoxy, isooctoxy, 2-ethylhexoxy, n-nonoxy or isononoxy.

$C_1$- to $C_4$-alkoxy comprises straight-chain or branched $C_1$- to $C_4$-alkoxy groups or cyclic $C_3$-alkoxy groups. $C_1$- to $C_4$-alkoxy is, for example, methoxy, ethoxy, n-propoxy, isopropoxy, cyclopropoxy, n-butoxy, sec-butoxy, isobutoxy or tert-butoxy.

In addition to 2,4,4-trimethylpent-2-ene, mixtures of 2,4,4-trimethylpent-1-ene and 2,4,4-trimethylpent-2-ene can also be used in the process according to the invention. If mixtures of 2,4,4-trimethylpent-1-ene and 2,4,4-trimethylpent-2-ene are used in the process according to the invention, both isomers are hydroformylated with high yields over time to give 3,5,5-trimethylhexanal.

Mixtures of 2,4,4-trimethylpent-1-ene and 2,4,4-trimethylpent-2-ene are preferably used when the 2,4,4-trimethylpent-2-ene to be hydroformylated originates from the dimerization of isobutene and is thus produced together with 2,4,4-trimethylpent-1-ene.

Due to the different dimerization processes for isobutene and/or the different purification processes for the diisobutene obtained from the dimerization, the composition of the mixtures may vary over wide ranges, depending on the preparation and/or purification process.

Mixtures of 2,4,4-trimethylpent-1-ene and 2,4,4-trimethylpent-2-ene preferably have a ratio of 2,4,4-trimethylpent-1-ene to 2,4,4-trimethylpent-2-ene in the range from 99:1 to 1:99, particularly preferably in the range from 95:5 to 5:95, further preferably in the range from 80:20 to 20:80 and especially preferably in the range from 80:20 to 70:30, for example a ratio of 75:25.

The molar ratio between the total amount of olefin and the total amount of rhodium in the reaction zone is preferably from 10 000:1 to 10:1 and more preferably from 5000:1 to 100:1.

The total amount of 2,4,4-trimethylpent-1-ene and 2,4,4-trimethylpent-2-ene in the total amount of olefin in the feed to the reaction zone is preferably 10 to 100%, particularly preferably 50 to 100% and especially preferably 90 to 100%. In addition to 2,4,4-trimethylpent-1-ene and 2,4,4-trimethylpent-2-ene, other olefins may also be present in the feed to the reaction zone and may be hydroformylated. Examples of such olefins are butenes, such as n-butene, 2-butene, isobutene and/or oligomers, such as can be formed in isobutene dimerization, for example 2,3,4-trimethylpentenes.

The hydroformylation takes place in a reaction zone comprising one or more identical or different reactors. In the simplest case, the reaction zone is formed by a single reactor. If there are two or more reactors, the reactors may have the same or different mixing characteristics. The reactors used can be divided once or more than once by internals. If a reaction zone is formed by more than one reactor, the reactors can be connected to one another as desired. For example, the reactors can be connected in parallel or in series. In principle, all reactor types that are suitable for hydroformylation reactions are suitable as reactors, such as stirred reactors, bubble column reactors as described, for example, in U.S. Pat. No. 4,778,929 A, circulation reactors as described, for example, in EP 11140017 A1, tubular reactors, wherein the individual reactors of a series may have different mixing characteristics, as described for example in EP 423769 A1 or compartmentalized reactors as described for example in EP 1231198 A1 or U.S. Pat. No. 5,728,893 A.

In the process according to the invention, the temperature in the reaction zone is 50 to 200° C. The temperature in the reaction zone in the process according to the invention is preferably 80 to 150° C. and particularly preferably 90 to 120° C.

In the process according to the invention, the pressure in the reaction zone is 1 to 100 bar abs. The pressure in the reaction zone in the process according to the invention is preferably 5 to 80 bar abs, more preferably 5 to 55 bar abs and particularly preferably 8 to 20 bar abs.

The rhodium catalyst homogeneously dissolved in the reaction medium is preferably formed in situ in the reaction zone by reacting a rhodium precursor with one or more organophosphite ligands of the general formula (I), CO and $H_2$.

Likewise preferably, the rhodium catalyst may also be used preformed. For this purpose, the rhodium catalyst is formed by reacting a rhodium precursor with one or more organophosphite ligands of the general formula (I), CO and $H_2$. The rhodium catalyst is preferably preformed at a temperature of 50 to 200° C., more preferably at a temperature of 80 to 150° C. and particularly preferably at a temperature of 90 to 120° C. The pressure during the preforming is preferably 1 to 100 bar abs, more preferably 5 to 80 bar abs, more preferably 5 to 55 bar abs and particularly preferably 8 to 20 bar abs. In particularly preferred cases, the preforming is carried out at a temperature and pressure comparable to that of the hydroformylation reaction itself. The rhodium precursor is preferably dissolved in a solvent. Examples of suitable solvents are aromatics such as toluene or xylenes, relatively long-chain hydrocarbons that are liquid under the reaction conditions, esters of aliphatic carboxylic acids with alkanols such as Texanol®, esters of aromatic carboxylic acids such as $C_8$- to $C_{13}$-dialkyl terephthalates or mixtures of two or more of the aforementioned solvents. The preforming can take place in the subsequent reaction zone or in a separate reactor. If the preforming takes place in the later reaction zone, the olefins to be hydroformylated are fed to the reaction zone when the preforming of the rhodium catalyst has at least largely taken place.

Preferred rhodium precursors are rhodium carbonyls, rhodium (I) salts, rhodium (II) salts, rhodium (III) salts or mixtures of two or more of the aforementioned precursors. Preferred rhodium carbonyls are $Rh_4(CO)_{12}$, $Rh_6(CO)_{16}$ or mixtures thereof. Preferred rhodium (I) salts are $Rh(CO)_2acac$, $Rh_2(CO)_4Cl_2$ or mixtures thereof. A preferred rhodium (II) salt is $Rh_2(OAc)_4$. A preferred rhodium (III) salt is $Rh(NO_3)_3$.

Rhodium precursor and organophosphite ligand of the general formula (I) may be fed to the reaction zone together or separately. Rhodium precursor and/or organophosphite ligand of the general formula (I) may be fed to the reaction zone directly or dissolved in a solvent. The solvent is, for example, 3,5,5-trimethylhexanal or higher-boiling reaction components, e.g. the products of the aldol condensation of 3,5,5-trimethylhexanal, aromatics such as toluene or xylenes, longer-chain hydrocarbons that are liquid under the reaction conditions, esters of aliphatic carboxylic acids with alkanols such as Texanol®, esters of aromatic carboxylic acids such as $C_8$- to $C_{13}$-dialkyl terephthalates or mixtures of two or more of the aforementioned solvents.

The rhodium concentration in the reaction zone is preferably in the range of 20 to 250 ppm by weight and particularly preferably in the range of 60 to 200 ppm by weight, based on the total weight of the liquid phase in the reaction zone.

Methods for supplementing rhodium in the reaction zone to compensate for a decrease in catalyst activity are described, for example, in U.S. Pat. No. 6,700,021 A or in EP 2836474 A1, the method described in EP 2836474 A1 being preferred.

The molar ratio of the total amount of organophosphite ligands of the general formula (I) in the reaction zone to the total amount of rhodium in the reaction zone is preferably in the range from 1:1 to 100:1 and particularly preferably in the range from 2:1 to 50:1, for example at 20:1 or at 10:1.

Free organophosphite ligands of the general formula (I) are homogeneously distributed in the reaction medium in the reaction zone. Free organophosphite ligands of the general formula (I) are not complexed with rhodium or other metals.

The molar ratio of $H_2$ to CO fed to the reaction zone is preferably from 2:1 to 1:2 and preferably from 60:40 to 50:50.

$H_2$ and CO are usually fed to the reaction zone as a gas mixture. In addition to $H_2$ and CO, the gas mixture may comprise other compounds such as $CH_4$, $N_2$, $CO_2$ and/or $H_2S$. The content of compounds other than $H_2$ and CO in the gas mixture is preferably less than 5% by volume.

The process according to the invention is preferably carried out in a solvent. The use of a solvent has the advantage that the heat of reaction generated during the hydroformylation is better distributed, thereby avoiding "hot spots" in the reaction zone. As a result, side reactions such as the degradation of the catalyst or condensation reactions of the aldehydes can be reduced. Suitable solvents are inert under the reaction conditions and during the work-up of the reaction products, i.e. they do not undergo any undesirable reactions with the starting materials, reaction products, organophosphite ligands of the general formula (I), rhodium precursors and/or the catalyst, the catalyst metal or catalyst metal-ligand complexes. Suitable solvents are, for example, 3,5,5-trimethylhexanal or higher-boiling reaction components, e.g. the products from the aldol condensation of 3,5,5-trimethylhexanal. Also suitable are aromatics such as toluene or xylenes, relatively long-chain hydrocarbons that are liquid under the reaction conditions, esters of aliphatic carboxylic acids with alkanols such as Texanol®, esters of aromatic carboxylic acids such as $C_8$- to $C_{13}$-dialkyl terephthalates or mixtures of two or more of the aforementioned solvents.

The process according to the present invention can be carried out as a continuous or semi-continuous operation or as a batch operation. A continuous or semi-continuous process is preferred.

The hydroformylation products are preferably separated off from the discharge from the reaction zone via the liquid discharge process. The substantially liquid discharge from the reaction zone is fed to a rectification process, the hydroformylation products being obtained as top products. The hydroformylation products thus obtained may then be fed to further work-up and/or reprocessing steps, for example hydrogenation or oxidation. It is preferred that the substantially liquid discharge from the reaction zone is depressurized in one or more stages, the discharge from each depressurization stage being separated into a liquid and a gaseous phase. As a result, for example, by-products which boil more readily than the hydroformylation products, unreacted olefin, hydrogen and/or carbon monoxide can be removed from the hydroformylation discharge.

The gaseous phase and the liquid phase obtained in the last depressurization stage are then fed in countercurrent to a rectification column. The hydroformylation products are mainly obtained in the top fraction. The high-boiling by-products are obtained, together with the catalyst metal-ligand complexes and possibly their degradation products, predominantly in the bottom fraction. The high-boiling by-products and the catalyst metal-ligand complexes dissolved therein, and optionally their degradation products, can be recycled into the hydroformylation reaction, or to the processing of the catalyst metal. Advantageous process configurations for the liquid discharge process are disclosed, for example, in EP 0846095 A1 or EP 1255720 A1. The crude hydroformylation products obtained in the top fraction can then be passed on for further processing. A suitable process for the purification by distillation of the crude hydroformylation products obtained in the top fraction is described, for example, in DE 19914260 A1. Even if the process disclosed in DE 19914260 A1 is restricted to alcohols, it is within the capability of those skilled in the art to apply the process to the purification by distillation of the crude hydroformylation products.

Preferred Embodiments of the Invention are

1. A hydroformylation process for preparing 3,5,5-trimethylhexanal comprising reacting 2,4,4-trimethylpent-2-ene with $H_2$ and CO in a reaction zone in the presence of one or more free organophosphite ligands of the general formula (I)

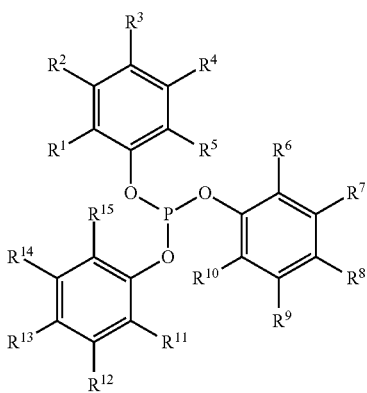

Formula (I)

wherein
$R^1$, $R^2$, $R^3$, $R^4$ and $R^5$ are each independently H, $C_1$- to $C_9$-alkyl or $C_1$- to $C_9$-alkoxy and $R^1$, $R^2$, $R^3$, $R^4$ and $R^5$ are not H at the same time, and
$R^6$, $R^7$, $R^8$, $R^9$ and $R^{10}$ are each independently H, $C_1$- to $C_9$-alkyl or $C_1$- to $C_9$-alkoxy and $R^6$, $R^7$, $R^8$, $R^9$ and $R^{10}$ are not H at the same time, and
$R^{11}$, $R^{12}$, $R^{13}$, $R^{14}$ and $R^{15}$ are each independently H, $C_1$- to $C_9$-alkyl or $C_1$- to $C_9$-alkoxy and $R^{11}$, $R^{12}$, $R^{13}$, $R^{14}$ and $R^{15}$ are not H at the same time,
and a homogeneous rhodium catalyst complexed with one or more organophosphite ligands of the general formula (I) at a pressure of 1 to 100 bar abs and a temperature of from 50 to 200° C.

2. The process according to embodiment 1, wherein a mixture comprising 2,4,4-trimethylpent-1-ene and 2,4,4-trimethylpent-2-ene is converted to 3,5,5-trimethylhexanal.

3. The process according to embodiment 2, wherein the ratio of 2,4,4-trimethylpent-1-ene to 2,4,4-trimethylpent-2-ene in the mixture used is in the range from 99:1 to 1:99, preferably in the range from 95:5 to 5:95, further preferably in the range from 80:20 to 20:80 and particularly preferably in the range from 80:20 to 70:30, and for example 75:25.

4. The process according to any of embodiments 1 to 3, wherein the total amount of 2,4,4-trimethylpent-1-ene and 2,4,4-trimethylpent-2-ene of the total amount of olefin in the feed to the reaction zone is from 10 to 100%, preferably 50 to 100% and particularly preferably 90 to 100%.

5. The process according to any of embodiments 1 to 4, wherein the hydroformylation is carried out at a temperature of 80 to 150° C.

6. The process according to any of embodiments 1 to 4, wherein the hydroformylation is carried out at a temperature of 90 to 120° C.

7. The process according to any of embodiments 1 to 6, wherein the hydroformylation is carried out at a pressure of 5 to 80 bar abs.

8. The process according to any of embodiments 1 to 6, wherein the hydroformylation is carried out at a pressure of 5 to 55 bar abs.

9. The process according to any of embodiments 1 to 6, wherein the hydroformylation is carried out at a pressure of 8 to 20 bar abs.

10. The process according to any of embodiments 1 to 9, wherein the molar ratio of the total amount of organophosphite ligands of the general formula (I) in the reaction zone to the total amount of rhodium in the reaction zone is in the range from 1:1 to 100:1.

11. The process according to any of embodiments 1 to 9, wherein the molar ratio of the total amount of organophosphite ligands of the general formula (I) in the reaction zone to the total amount of rhodium in the reaction zone is in the range from 2:1 to 50:1.

12. The process according to any of embodiments 1 to 11, wherein the rhodium concentration in the reaction zone is in the range of 20 to 250 ppmw based on the total weight of the liquid phase in the reaction zone.

13. The process according to any of embodiments 1 to 11, wherein the rhodium concentration in the reaction zone is in the range of 60 to 200 ppmw based on the total weight of the liquid phase in the reaction zone.

14. The process according to any of embodiments 1 to 13, wherein the one or more organophosphite ligands of the general formula (I) are one or more of the following compounds:

| Organophosphite ligand of the general formula (I) | $R^1$, $R^6$, $R^{11}$ | $R^3$, $R^8$, $R^{13}$ | $R^2$, $R^4$, $R^5$, $R^7$, $R^9$, $R^{10}$, $R^{12}$, $R^{14}$, $R^{15}$ |
|---|---|---|---|
| I) | Methyl | Methyl | H |
| II) | Methyl | H | H |
| III) | Ethyl | Ethyl | H |
| IV) | Ethyl | H | H |
| V) | n-Propyl | n-Propyl | H |
| VI) | n-Propyl | H | H |
| VII) | Isopropyl | Isopropyl | H |
| VIII) | Isopropyl | H | H |
| IX) | n-Butyl | n-Butyl | H |
| X) | n-Butyl | H | H |
| XI) | sec-Butyl | sec-Butyl | H |
| XII) | sec-Butyl | H | H |
| XIII) | Isobutyl | Isobutyl | H |
| XIV) | Isobutyl | H | H |
| XV) | tert-Butyl | tert-Butyl | H |
| XVI) | tert-Butyl | H | H |
| XVII) | Methoxy | Methoxy | H |
| XVIII) | Methoxy | H | H |
| XIX) | Ethoxy | Ethoxy | H |
| XX) | n-Propoxy | n-Propoxy | H |
| XXI) | n-Propoxy | H | H |
| XXII) | Isopropoxy | Isopropoxy | H |
| XXIII) | Isopropoxy | H | H |
| XXIV) | n-Butoxy | n-Butoxy | H |
| XXV) | n-Butoxy | H | H |
| XXVI) | sec-Butoxy | sec-Butoxy | H |
| XXVII) | sec-Butoxy | H | H |
| XXVIII) | Isobutoxy | Isobutoxy | H |
| XXIX) | Isobutoxy | H | H |
| XXX) | tert-Butoxy | tert-Butoxy | H |
| XXXI) | tert-Butoxy | H | H |
| XXXII) | n-Nonyl | H | H |

15. The process according to any of embodiments 1 to 14, wherein the molar ratio of $H_2$ to CO fed to the reaction zone is from 2:1 to 1:2 and preferably from 60:40 to 50:50.

16. The process according to any of embodiments 1 to 15, wherein the rhodium catalyst is at least partially formed in the reaction zone by reacting a rhodium precursor with one or more organophosphite ligands of the general formula (I), as defined in either of embodiments 1 or 14, CO and $H_2$.

17. The process according to embodiment 16, wherein the rhodium precursor is rhodium carbonyls, rhodium (I) salts, rhodium (II) salts, rhodium (III) salts or mixtures of two or more of the aforementioned precursors.

18. The process according to embodiment 17, wherein rhodium carbonyls are $Rh_4(CO)_{12}$, $Rh_2(CO)_{16}$ or mixtures thereof.

19. The process according to embodiment 17, wherein the rhodium (I) salts are $Rh(CO)_2acac$, $Rh_2(CO)_4Cl_2$ or mixtures thereof.

20. The process according to embodiment 17, wherein the rhodium (II) salts are $Rh_2(OAc)$ 4.

21. The process according to embodiment 17, wherein the rhodium (III) salts are $Rh(NO_3)$ 3.

22. The process according to any of embodiments 1 to 15, wherein the rhodium catalyst is used at least partially preformed.

23. The process according to embodiment 22, wherein the rhodium catalyst is used preformed.

24. The process according to any of embodiments 1 to 23, wherein the process is carried out continuously.

25. The process according to any of embodiments 1 to 23, wherein the process is carried out batchwise.

EXAMPLES

Example 1

Under argon, $Rh(CO)_2$ (acac) (5.1 mg, 0.02 mmol) and tris(2,4-di-tert-butylphenyl) phosphite (640 mg, 0.99 mmol) were dissolved in diisobutene (20.0 g, 178 mmol; 2,4,4-trimethylpent-1-ene/2,4,4-trimethylpent-2-ene: 80:20 to 75:25) and filled into a 100 mL stainless steel autoclave under an argon countercurrent. Then ~5 bar $CO/H_2$ (1:1) was applied and the autoclave heated to 100° C. over 10 min. At this temperature, the pressure was increased to 10 bar and the contents were stirred for 10 hours. The autoclave was cooled to room temperature, depressurized to atmospheric pressure and an aliquot of the reaction discharge obtained analyzed by gas chromatography. GC-Method: Optimal column (30 m, d=320 μm, $F_d$=0.5 μm), temperature program: 50° C. for 2 min, at 5° C./min to 90° C. and for 2 min isothermally, at 20° C./min to 250° C., helium as carrier gas. tR (2,4,4-trimethylpent-1-ene)=5.27 min, tR (2,4,4-trimethylpent-2-ene)=5.77 min, tR (3,5,5-trimethylhexanal)=13.76 min).

The following result was achieved:
Conversion of diisobutene: >98%
Selectivity for 3,5,5-trimethylhexanal: 97.0%
Selectivity for 2,4,4-trimethylpentane: 3.0%

Example 2

Under argon, $Rh(CO)_2$ (acac) (5.1 mg, 0.02 mmol) and tris(2,4-di-tert-butylphenyl) phosphite (640 mg, 0.99 mmol) were dissolved in toluene (2.5 mL) and filled into a 100 mL stainless steel autoclave. Then, 10 bar $CO/H_2$ (1:1) was applied, the mixture heated to 100° C. over 10 min and stirred for 1 h. At this temperature, diisobutene (20.0 g, 178 mmol, 2,4,4-trimethylpent-1-ene/2,4,4-trimethylpent-2-ene: 80:20 to 75:25) was added in countercurrent and the mixture stirred for 6 h. The autoclave was cooled to room temperature, depressurized to atmospheric pressure and an aliquot of the reaction discharge obtained analyzed by gas chromatography. GC-Method: Optimal column (30 m, d=320 μm, $F_d$=0.5 μm), temperature program: 50° C. for 2 min, at 5° C./min to 90° C. and for 2 min isothermally, at 20° C./min to 250° C., helium as carrier gas. tR (2,4,4-trimethylpent-1-ene)=5.27 min, tR (2,4,4-trimethylpent-2-ene)=5.77 min, tR (3,5,5-trimethylhexanal)=13.76 min).

The following result was achieved:
Conversion of diisobutene: >95%
Selectivity for 3,5,5-trimethylhexanal: 97.0%
Selectivity for 2,4,4-trimethylpentane: 3.0%

Example 3

Under argon, $Rh(CO)_2$ (acac) (5.1 mg, 0.02 mmol) and tris(2,4-di-tert-butylphenyl) phosphite (640 mg, 0.99 mmol) were dissolved in 2,4,4-trimethylpent-2-ene (20.0 g, 178 mmol) and filled into a 100 mL stainless steel autoclave under an argon countercurrent. Then ~5 bar $CO/H_2$ (1:1) was applied and the autoclave heated to 100° C. over 10 min. At this temperature, the pressure was increased to 10 bar and the contents were stirred for 10 hours. The autoclave was cooled to room temperature, depressurized to atmospheric pressure and an aliquot of the reaction discharge obtained analyzed by gas chromatography. GC-Method: Optimal column (30 m, d=320 μm, $F_d$=0.5 μm), temperature program: 50° C. for 2 min, at 5° C./min to 90° C. and for 2 min isothermally, at 20° C./min to 250° C., helium as carrier gas. tR (2,4,4-trimethylpent-1-ene)=5.27 min, tR (2,4,4-trimethylpent-2-ene)=5.77 min, tR (3,5,5-trimethylhexanal)=13.76 min).

The following result was achieved:
Conversion of diisobutene: >85%
Selectivity for 3,5,5-trimethylhexanal: 96.0%
Selectivity for 2,4,4-trimethylpentane: 4.0%

Example 4

A solution of tris(2,4-di-tert-butylphenyl) phosphite L1 in 3,5,5-trimethylhexanal (10% by weight) was stirred under reflux under argon. After 1 d, 5 d, 8 d, 12 d, 21 d and 27 d, samples were analyzed by $^{31}$P-NMR spectroscopy (tris(2,4-di-tert-butylphenyl) phosphite: δ=129.9 ppm; tris(2,4-di-tert-butylphenyl) phosphate δ=−20.0 ppm).

The following result was achieved:

| Reaction time | $^{31}$P-NMR (129.9 ppm) | $^{31}$P-NMR (−20.0 ppm) |
|---|---|---|
| 1 d | >99% | <1% |
| 5 d | >99% | <1% |
| 8 d | 99% | 1% |
| 12 d | 98% | 2% |
| 21 d | 97% | 3% |
| 27 d | 97% | 3% |

As the example shows, the ligand has high stability in the reaction product. The high stability of the ligand ensures a long service life for the process. Furthermore, the high stability of the ligands has the advantage that the formation of by-products is reduced. In addition, the ligands and/or the catalyst metal-ligand complex can be recycled into the process in the case of a continuous process regime due to their high stability.

The examples serve to illustrate the present invention. The examples do not limit the present invention.

The invention claimed is:

1. A hydroformylation process for preparing 3,5,5-trimethylhexanal comprising reacting 2,4,4-trimethylpent-2-ene with $H_2$ and CO in a reaction zone in the presence of one or more free organophosphite ligands of general formula (I)

Formula (I)

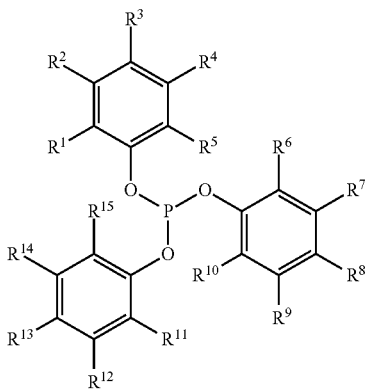

wherein,
$R^1$, $R^2$, $R^3$, $R^4$ and $R^5$ are each independently H, $C_1$- to $C_9$-alkyl or $C_1$- to $C_9$-alkoxy and $R^1$, $R^2$, $R^3$, $R^4$ and $R^5$ are not H at the same time, and
$R^6$, $R^7$, $R^8$, $R^9$ and $R^{10}$ are each independently H, $C_1$- to $C_9$-alkyl or $C_1$- to $C_9$-alkoxy and $R^6$, $R^7$, $R^8$, $R^9$ and $R^{10}$ are not H at the same time, and
$R^{11}$, $R^{12}$, $R^{13}$, $R^{14}$ and $R^{15}$ are each independently H, $C_1$- to $C_9$-alkyl or $C_1$- to $C_9$-alkoxy and $R^{11}$, $R^{12}$, $R^{13}$, $R^{14}$ and $R^{15}$ are not H at the same time,
and a homogeneous rhodium catalyst complexed with one or more organophosphite ligands of the general formula (I) at a pressure of 1 to 100 bar abs and a temperature of from 50 to 200° C.

2. The process according to claim 1, wherein a mixture comprising 2,4,4-trimethylpent-1-ene and 2,4,4-trimethylpent-2-ene is converted to 3,5,5-trimethylhexanal.

3. The process according to claim 2, wherein the ratio of 2,4,4-trimethylpent-1-ene to 2,4,4-trimethylpent-2-ene in the mixture used is in the range from 99:1 to 1:99.

4. The process according to claim 1, wherein the total amount of 2,4,4-trimethylpent-1-ene and 2,4,4-trimethylpent-2-ene of the total amount of olefin in the feed to the reaction zone is from 10 to 100%.

5. The process according to claim 1, wherein the hydroformylation is carried out at a temperature of 80 to 150° C.

6. The process according to claim 1, wherein the hydroformylation is carried out at a pressure of 5 to 80 bar abs.

7. The process according to claim 1, wherein the molar ratio of the total amount of organophosphite ligands of the general formula (I) in the reaction zone to the total amount of rhodium in the reaction zone is in the range from 1:1 to 100:1.

8. The process according to claim 1, wherein the rhodium concentration in the reaction zone is in the range of 20 to 250 ppmw based on the total weight of the liquid phase in the liquid phase in the reaction zone.

9. The process according to claim 1, wherein the one or more organophosphite ligands of the general formula (I) are one or more of the following compounds:

| Organophosphite ligand of general formula (I) | $R^1$, $R^6$, $R^{11}$ | $R^3$, $R^8$, $R^{13}$ | $R^2$, $R^4$, $R^5$, $R^7$, $R^9$, $R^{10}$, $R^{12}$, $R^{14}$, $R^{15}$ |
|---|---|---|---|
| I) | Methyl | Methyl | H |
| II) | Methyl | H | H |
| III) | Ethyl | Ethyl | H |
| IV) | Ethyl | H | H |
| V) | n-Propyl | n-Propyl | H |
| VI) | n-Propyl | H | H |
| VII) | Isopropyl | Isopropyl | H |
| VIII) | Isopropyl | H | H |
| IX) | n-Butyl | n-Butyl | H |
| X) | n-Butyl | H | H |
| XI) | sec-Butyl | sec-Butyl | H |
| XII) | sec-Butyl | H | H |
| XIII) | Isobutyl | Isobutyl | H |
| XIV) | Isobutyl | H | H |
| XV) | tert-Butyl | tert-Butyl | H |
| XVI) | tert-Butyl | H | H |
| XVII) | Methoxy | Methoxy | H |
| XVIII) | Methoxy | H | H |
| XIX) | Ethoxy | Ethoxy | H |
| XX) | n-Propoxy | n-Propoxy | H |
| XXI) | n-Propoxy | H | H |
| XXII) | Isopropoxy | Isopropoxy | H |
| XXIII) | Isopropoxy | H | H |
| XXIV) | n-Butoxy | n-Butoxy | H |
| XXV) | n-Butoxy | H | H |
| XXVI) | sec-Butoxy | sec-Butoxy | H |
| XXVII) | sec-Butoxy | H | H |
| XXVIII) | Isobutoxy | Isobutoxy | H |
| XXIX) | Isobutoxy | H | H |
| XXX) | tert-Butoxy | tert-Butoxy | H |
| XXXI) | tert-Butoxy | H | H |
| XXXII) | n-Nonyl | H | H. |

10. The process according to claim 1, wherein the molar ratio of $H_2$ to CO fed to the reaction zone is from 2:1 to 1:2.

11. The process according to claim 1, wherein the rhodium catalyst is at least partially formed in the reaction zone by reacting a rhodium precursor with one or more organophosphite ligands of the general formula (I), CO and $H_2$.

12. The process according to claim 11, wherein the rhodium precursor is rhodium carbonyls, rhodium (I) salts, rhodium (II) salts, rhodium (III) salts or mixtures of two or more of the aforementioned precursors.

13. The process according to claim 1, wherein the rhodium catalyst is used at least partially preformed.

14. The process according to claim 1, wherein the method is carried out continuously.

\* \* \* \* \*